United States Patent
Sung et al.

(10) Patent No.: US 11,987,820 B2
(45) Date of Patent: May 21, 2024

(54) SALT-LOVING BACILLUS POLYFERMENTICUS STRAIN FOR PRODUCING SALT-TOLERANT GAMMA-GLUTAMYL TRANSPEPTIDASE

(71) Applicant: KOOKMINBIO, CORP., Jeollabuk-do (KR)

(72) Inventors: Moon Hee Sung, Seoul (KR); Misun Kwak, Goyang-si (KR); Seon-Young Baek, Ulsan (KR)

(73) Assignee: KOOKMINBIO, CORP., Jeollabuk-do (KR)

( * ) Notice: Subject to any disclaimer, the term of this patent is extended or adjusted under 35 U.S.C. 154(b) by 781 days.

(21) Appl. No.: 17/255,419

(22) PCT Filed: May 9, 2019

(86) PCT No.: PCT/KR2019/005584
§ 371 (c)(1),
(2) Date: Jul. 11, 2021

(87) PCT Pub. No.: WO2020/004809
PCT Pub. Date: Jan. 2, 2020

(65) Prior Publication Data
US 2021/0371830 A1    Dec. 2, 2021

(30) Foreign Application Priority Data

Jun. 26, 2018 (KR) .................. 10-2018-0073513
Jan. 29, 2019 (KR) .................. 10-2019-0011215

(51) Int. Cl.
*C12N 9/10*     (2006.01)
*A23L 33/135*   (2016.01)
*C12R 1/07*     (2006.01)

(52) U.S. Cl.
CPC ............ *C12N 9/104* (2013.01); *A23L 33/135* (2016.08); *C12Y 203/02002* (2013.01); *A23V 2002/00* (2013.01); *C12R 2001/07* (2021.05)

(58) Field of Classification Search
CPC .................. C12N 9/104; A23L 33/135; C12Y 203/02002
See application file for complete search history.

(56) References Cited

U.S. PATENT DOCUMENTS

| | | |
|---|---|---|
| 5,153,120 A | 10/1992 | Katsumata et al. |
| 2003/0104064 A1 | 6/2003 | Sung et al. |
| 2022/0033797 A1* | 2/2022 | Sung ................. A23L 33/135 |

FOREIGN PATENT DOCUMENTS

| | | |
|---|---|---|
| EP | 0275901 A2 | 7/1988 |
| KR | 10-2001-0078440 A | 8/2001 |

(Continued)

OTHER PUBLICATIONS

International Search Report for PCT/KR2019/005584 mailed Aug. 19, 2019 from Korean Intellectual Property Office.

*Primary Examiner* — Anthony J Weier
(74) *Attorney, Agent, or Firm* — Revolution IP, PLLC (57) ABSTRACT

The present invention relates to a halophilic *Bacillus polyfermenticus* KMU01 strain producing salt-tolerant gamma-glutamyl transpeptidase, and the halophilic *Bacillus polyfermenticus* KMU01 strain according to the present invention (KCTC11751BP) producing a halophilic gamma-glutamyl transpeptidase, wherein, when food is fermented using the strain of the present invention, it can be utilized in foods with high salt concentration, and fermented foods having excellent flavor and various peptides can be prepared by high enzyme activity that decomposes protein binding.

9 Claims, 9 Drawing Sheets

(56) References Cited

FOREIGN PATENT DOCUMENTS

| KR | 10-2001-0084684 A | 9/2001 |
|----|-------------------|--------|
| KR | 10-2012-0131349 A | 12/2012 |
| KR | 10-2013-0095127 A | 8/2013 |
| KR | 10-2017-0003289 A | 1/2017 |
| KR | 10-1814024 B1 | 1/2018 |

* cited by examiner

RECEIPT IN THE CASE OF AN ORIGINAL DEPOSIT

TO: SUNG, Moon-Hee
Kookmin University
861-1 Jeongneung-dong, Seongbuk-gu, Seoul 136-702
Republic of Korea

| I. IDENTIFICATION OF THE MICROORGANISM | |
|---|---|
| Identification reference given by the DEPOSITOR:<br>*Bacillus amyloliquefaciens* Kimchi | Accession number given by the INTERNATIONAL DEPOSITARY AUTHORITY:<br>KCTC 11751BP |
| II. SCIENTIFIC DESCRIPTION AND/OR PROPOSED TAXONOMIC DESIGNATION | |
| The microorganism identified under I above was accompanied by:<br>[x] a scientific description<br>[ ] a proposed taxonomic designation<br>(Mark with a cross where applicable) | |
| III. RECEIPT AND ACCEPTANCE | |
| This International Depositary Authority accepts the microorganism identified under I above, which was received by it on August 25, 2010. | |
| IV. RECEIPT OF REQUEST FOR CONVERSION | |
| The microorganism identified under I above was received by this International Depositary Authority on     and a request to convert the original deposit to a deposit under the Budapest Treaty was received by it on | |
| V. INTERNATIONAL DEPOSITARY AUTHORITY | |
| Name: Korean Collection for Type Cultures<br>Address: Korea Research Institute of Bioscience and Biotechnology (KRIBB)<br>111 Gwahangno, Yuseong-gu, Daejeon 305-806 Republic of Korea | Signature(s) of person(s) having the power to represent the International Depositary Authority of authorized official(s):<br>Director: LEE, Jung-Sook,<br>August 31, 2010 |

| There is no difference from the original translation above | |

FIG. 7

ATTESTATION CONCERNING THE LATER INDICATION OR
AN AMENDMENT OF THE SCIENTIFIC DESCRIPTION
AND/OR PROPOSED TAXONOMIC DESIGNATION

TO: SUNG, Moon-Hee
Kookmin University
77, Jeongneung-ro, Seongbuk-gu, Seoul 02707
Republic of Korea

| The enclosed communication has been received by this INTERNATIONAL DEPOSITARY AUTHORITY on August 25, 2010.<br><br>KCTC 11751BP<br>*Bacillus amyloliquefaciens* Kimchi → *Bacillus polyfermenticus* KMU01 |
|---|

| V. INTERNATIONAL DEPOSITARY AUTHORITY | |
|---|---|
| Name: Korean Collection for Type Cultures<br>Address: Korea Research Institute of Bioscience and Biotechnology (KRIBB) 181, Ipsin-gil, Jeongeup-si, Jeollabuk-do 56212 Republic of Korea | Signature(s) of person(s) having the power to represent the International Depositary Authority of authorized official(s):<br>Director: KIM, Cha Young<br>June 27, 2018 |

Enclosure: Communication of the later indication or an amendment of the scientific description and proposed taxonomic designation pursuant to Rule 8.1

| There is no difference from the original translation above | |
|---|---|

SALT-LOVING BACILLUS POLYFERMENTICUS STRAIN FOR PRODUCING SALT-TOLERANT GAMMA-GLUTAMYL TRANSPEPTIDASE

CROSS REFERENCE TO PRIOR APPLICATIONS

This application is the 35 U.S.C. 371 national stage of International application PCT/KR2019/005584 filed on May 9, 2019; which claims priority to Korean application 10-2018-0073513 filed on Jun. 26, 2018, and Korean application 10-2019-0011215 filed on Jan. 29, 2019. The entire contents of each of the above-identified applications are hereby incorporated by reference.

TECHNICAL FIELD

The present invention relates to a novel halophilic *Bacillus polyfermenticus* KMU01 strain producing a salt-tolerant gamma-glutamyl transpeptidase and a method of preparing a gamma-glutamyl transpeptidase using the same.

BACKGROUND ART

Gamma-glutamyl transpeptidase is an enzyme which breaks glutamyl bonds in substances such as glutathione to transfer a part of glutamyl to water as the hydrolysis action or transfer a part of glutamyl to other amino acids or peptides as transpeptidation action. This enzyme is involved in the metabolism of glutathione and plays an important role in antioxidant defense, detoxification and inflammatory reactions. In addition, this enzyme can be used in the food industry. For example, the effect of improving the bitter taste of amino acids and enhancing the umami taste of fermented foods has been proven, and can be used in various ways in the food industry.

As an enzyme-producing strain that produces gamma-glutamyl transpeptidase, a halophilic (salt-loving) strain has also high availability. *Bacillus* strains play an important role in the initial fermentation of kimchi, a fermented food. The reason is that enzymes produced by *Bacillus* strains break down proteins in kimchi and salted fish to produce useful peptides, and play a role in enhancing the flavor of kimchi. Because kimchi is fermented using salt and salted fish, salt concentration thereof is higher than that of general foods. Therefore, the halophilic *Bacillus* strain has a wide range of action in a fermentation environment with a high salt concentration. Until now, enzymes with high activity have been mainly explored and developed, and there are not many examples of halophilic *Bacillus*. Therefore, it is considered that the halophilic *Bacillus* strain producing a halophilic enzyme will have a wide application value in the food field.

DISCLOSURE

Technical Problem

An object of the present invention is to provide a halophilic *Bacillus polyfermenticus* KMU01 strain producing a salt-tolerant gamma-glutamyl transpeptidase (KCTC11751BP), a method of preparing salt-tolerant gamma-glutamyl transpeptidase using the same and a food composition comprising a bacterial body, a culture obtained by culturing the strain, or a salt-tolerant gamma-glutamyl transpeptidase isolated and purified therefrom as an active ingredient.

Technical Solution

In order to achieve the above object, the present invention provides a halophilic *Bacillus polyfermenticus* KMU01 strain producing salt-tolerant gamma-glutamyl transpeptidase (KCTC11751BP).

Also, the present invention provides a method of preparing salt-tolerant gamma-glutamyl transpeptidase comprising culturing the halophilic *Bacillus polyfermenticus* KMU01 strain.

In addition, the present invention provides a food composition comprising a bacterial body, culture obtained by culturing the halophilic *Bacillus polyfermenticus* KMU01 strain, culture or the salt-tolerant gamma-glutamyl transpeptidase isolated and purified therefrom as an active ingredient.

Advantageous Effects

The present invention relates to a halophilic *Bacillus polyfermenticus* KMU01 strain producing salt-tolerant gamma-glutamyl transpeptidase, and the halophilic *Bacillus polyfermenticus* KMU01 strain according to the present invention (KCTC11751BP) produces a halophilic gamma-glutamyl transpeptidase. When food is fermented using the strain of the present invention, it can be used in foods with high salt concentration, and fermented foods having excellent flavor and various peptides can be produced by high enzyme activity that decomposes protein binding.

BEST MODE

The present invention provides a halophilic *Bacillus polyfermenticus* KMU01 strain producing salt-tolerant gamma-glutamyl transpeptidase.

Preferably, the strain may be deposited with the Korea Research Institute of Bioscience and Biotechnology as KCTC11751BP, but it is not limited thereto.

Preferably, the strain may be grown at a concentration of 0.5 to 15% NaCl and a temperature of 30 to 40° C., more preferably, the strain may be grown optimally at a concentration of 5% NaCl and a temperature of 40° C., but it is not limited thereto.

Preferably, the gamma-glutamyl transpeptidase may exhibit an activity at a concentration of 0.5 to 15% NaCl and a temperature of 30 to 40° C. and more preferably, it may exhibit the highest activity at a concentration of 5% NaCl and a temperature of 40° C., but it is not limited thereto.

The *Bacillus polyfermenticus* KMU01 strain used in the present invention was deposited with the Korea Research Institute of Bioscience and Biotechnology as KCTC11751BP (accession date: Aug. 25, 2010) "*Bacillus amyloliquefaciens* Kimchi", but through a clear strain identification, the name was corrected as "*Bacillus polyfermenticus* KMU01".

In addition, the present invention provides a method of preparing salt-tolerant gamma-glutamyl transpeptidase comprising culturing the halophilic *Bacillus polyfermenticus* KMU01 strain.

Preferably, the strain culture may be cultured at a concentration of 0.5 to 15% NaCl and a temperature of 30 to 40° C., but it is not limited thereto.

In addition, the present invention provides a food composition comprising a bacterial body, a culture obtained by culturing the halophilic *Bacillus polyfermenticus* KMU01 strain, or a salt-tolerant gamma-glutamyl transpeptidase isolated and purified therefrom as an active ingredient.

In the case of the food composition of the present invention, there is no particular limitation on the kind of the food. Examples of foods to which can be added as the active ingredient, include meat, sausage, bread, chocolate, candy, snacks, confectionery, pizza, ramen, other noodles, gum, dairy products including ice cream, fermented products including kimchi and salted fish, various soups, beverages, teas, drinks, alcoholic beverages, vitamin complexes and the like.

Hereinafter, the present invention will be described in more detail through examples. These examples are only intended to illustrate the present invention in more detail, and it will be apparent to those skilled in the art that the scope of the present invention is not limited by these examples according to the gist of the present invention.

<Example 1> Identification of *Bacillus polyfermenticus* Strain

1. Isolation of Fermented Food Microorganisms

A fermented food, cutlass fish Kimchi, was purchased and *Bacillus* was separated from it. The fermented food was pulverized and 1 g of the fermented food is suspended in physiological saline, and 0.1 ml of the supernatant of the diluted suspension was smeared on TSA medium having 0.5%, 5%, and 10% of salt concentration (tryptone 1.7%, soytone 0.3%, dextrose 0.25%, sodium chloride 0.5%, dipotassium phosphate 0.25%, agar 1.5%), and cultured at 37° C. for 24 hours to separate. Among the cultured microorganisms, the bacteria with the best growth in a 10% salt concentration medium were selected.

2. Identification of Isolated Strains

Figure 1:
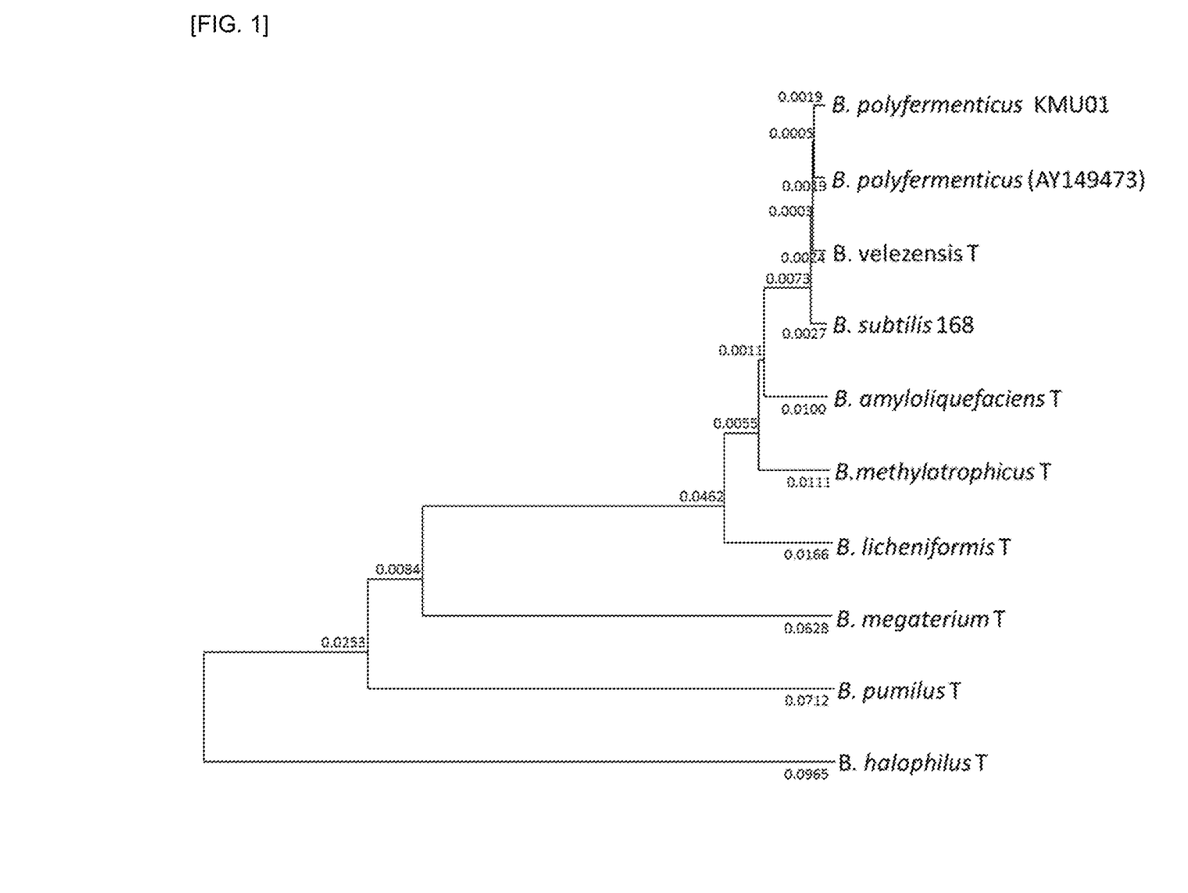
FIG. 1 shows the phylogenetic tree of the strain of the present invention.

DNA of the selected strain was extracted, 16s rRNA was amplified using 27F and 1492R primers, and the analyzed sequence information was identified using BLAST of NCBI (www.ncbi.nlm.nih.gov) to draw phylogenetic tree. As a result, the *Bacillus polyfermenticus* KMU01 strain of the present invention could be identified (FIG. 1).

<Example 2> Comparison of Halophilicity with Other Strains

Figure 2:
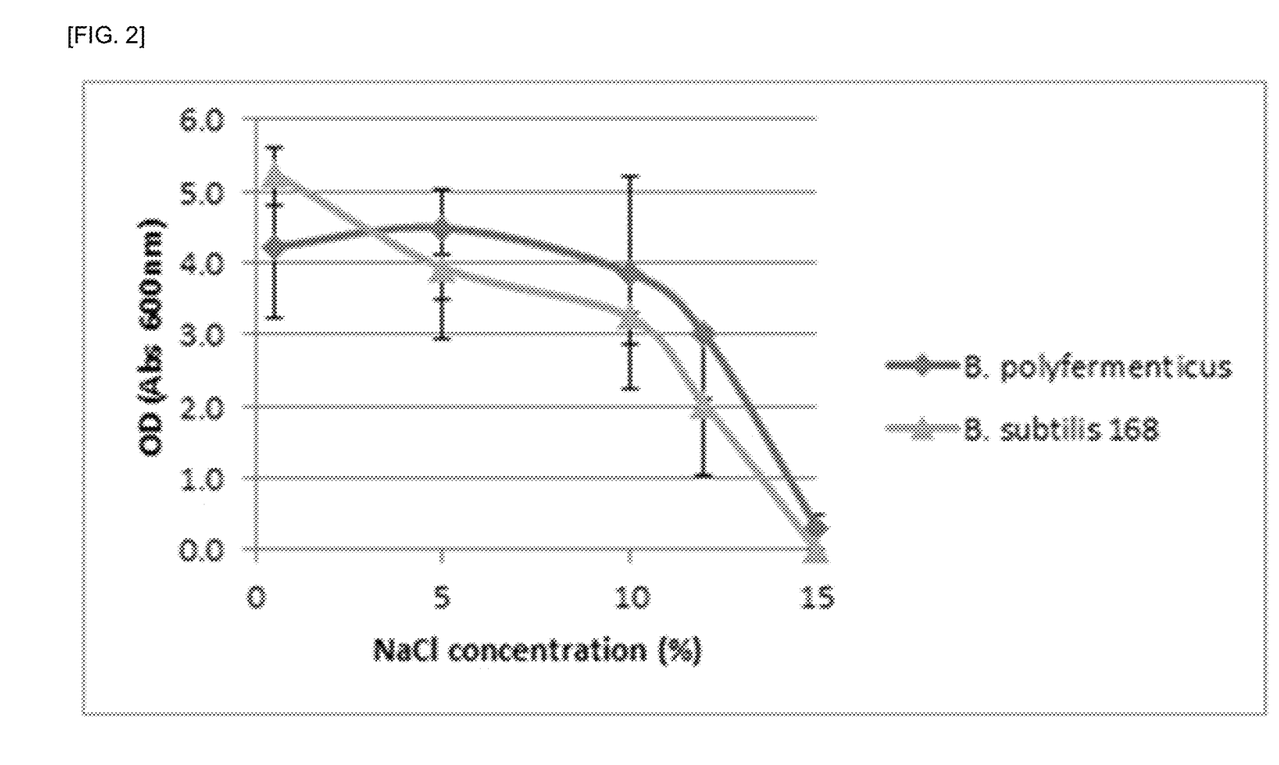
FIG. 2 shows a graph comparing sodium chloride resistance of "*Bacillus polyfermenticus*" and "*Bacillus subtilis* 168" of the present invention.

The strain according to the present invention and *Bacillus subtilis* 168 (*B. subtilis* 168) strain were cultured in TSB medium containing 0.5%, 5%, and 10% NaCl for 24 hours, and then the absorbance was measured at 600 nm for each strain to measure the degree of growth (FIG. 2). As shown in FIG. 2, it can be seen that the strain according to the present invention is resistant to sodium chloride by 10% or more compared to *Bacillus subtilis* 168.

<Example 3> Comparison of Gamma-Glutamyl Transpeptidase Activity with Other Strains The isolated strain was inoculated into 50 ml of TSB medium, and the supernatant of the culture solution cultured at 37° C. for 24 hours was taken and centrifuged at 8,000 rpm for 20 minutes. The amount of pNA produced was measured at 410 nm to analyze the enzyme activity. The activity of gamma-glutamyl transpeptidase was measured in the standard strains *Bacillus amyloliquefaciens* DSM7 strain and *Bacillus subtilis* 168 strain. *Bacillus amyloliquefaciens* DSM7 strain and *Bacillus subtilis* 168 strain were obtained from the Korean Collection for Type Cultures (KCTC).

Figure 3:
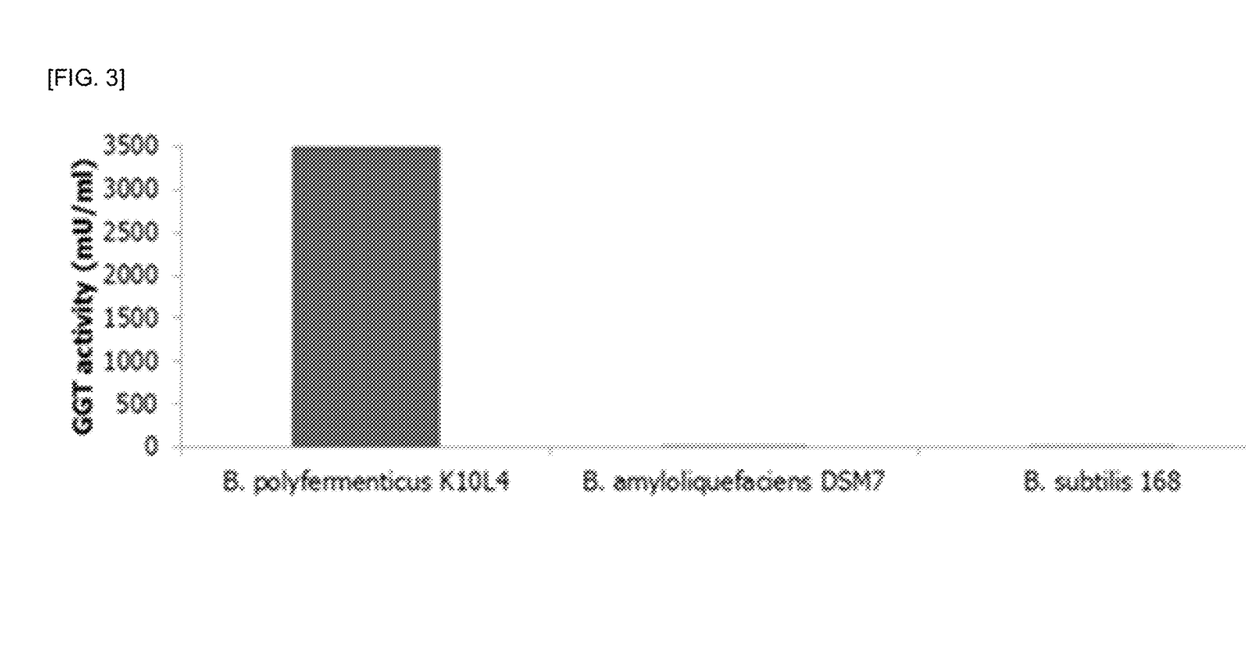
FIG. 3 shows a graph comparing gamma-glutamyl transpeptidase activity of the strain of the present invention and that of other strains.

As a result, it was found that the *Bacillus polyfermenticus* strain of the present invention exhibited an enzyme activity of about 3500 mU/ml or more, and was superior to other strains (Table 1, FIG. 3).

TABLE 1

| strain | gamma-glutamyl transpeptidase activity (mU/ml) |
|---|---|
| Bacillus polyfermenticus | 3,500 |
| Bacillus amyloliquefaciens DSM7 | 20 |
| Bacillus subtilis 168 | 10 |

<Example 4> Growth of Bacteria According to Culture Temperature and Salt Concentration In order to establish the optimal culture conditions of the strain, culture was performed at 200 rpm for 24 hours at various temperatures. The example was performed under temperature conditions of 30° C., 37° C. and 40° C., and under salt concentrations of 0.5% and 5%. After culturing for 24 hours, the growth of bacteria was measured at 600 nm.

Figure 4A:
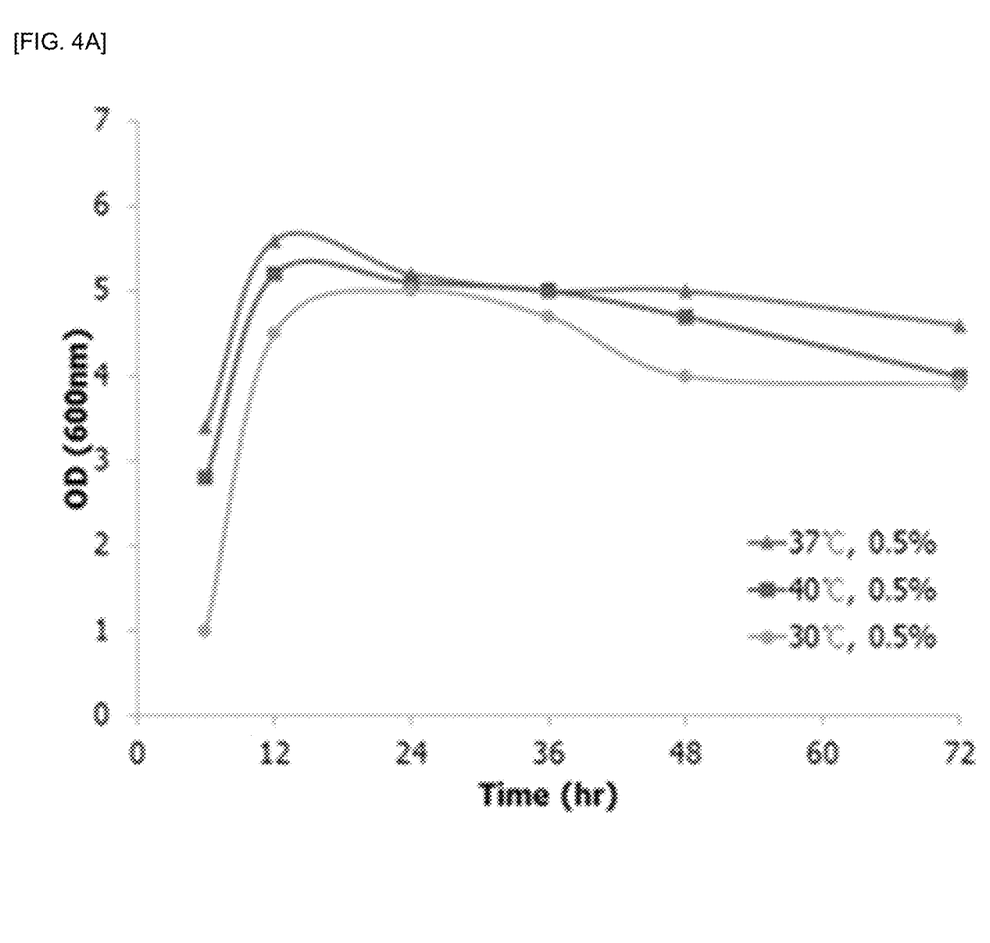
FIG. 4A shows the results of growth of bacteria by temperature in 0.5% sodium chloride medium
Figure 4B:
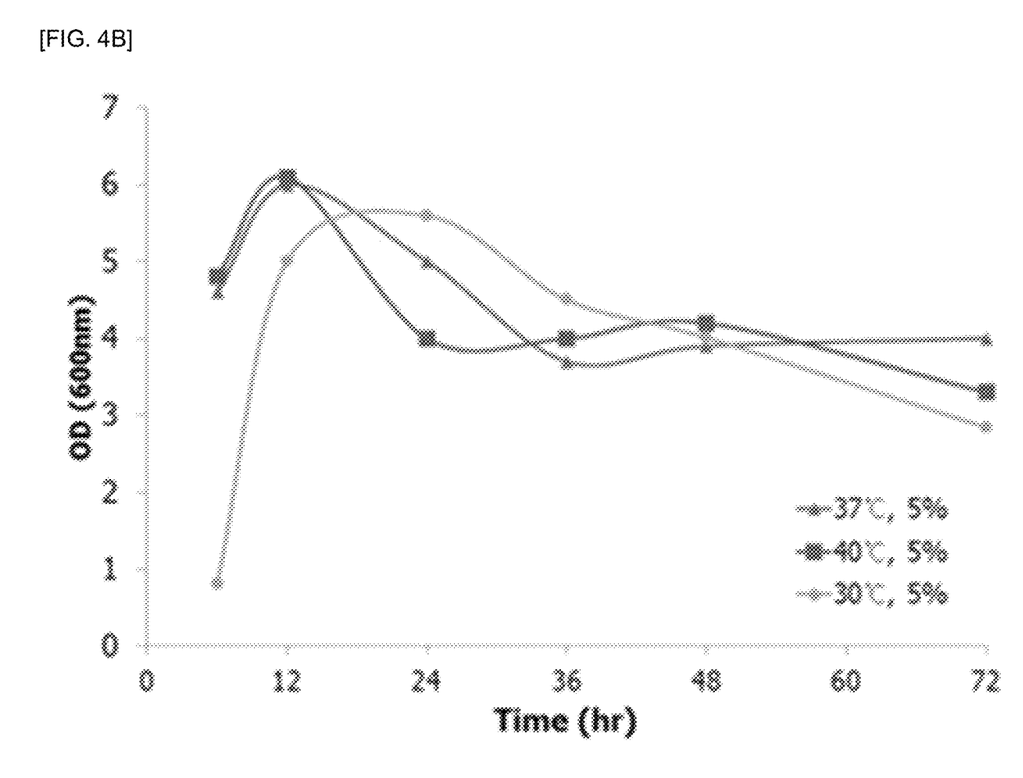
FIG. 4B shows the results of growth of bacteria by temperature in 5% sodium chloride medium.

FIG. 4A shows the growth of bacteria according to temperature in a 0.5% sodium chloride environment and FIG. 4B shows the growth of bacteria according to temperature in a 5% sodium chloride environment. The condition showing the maximum OD is 40° C. and 5% salt. From this, the strain shows optimal growth at 40° C. and 5% salt, and it can be said to be a halophilic bacteria as it shows optimal growth at a higher salt concentration than other strains.

<Example 5> Gamma-Glutamyl Transpeptidase Activity According to Culture Temperature and Salt Concentration In order to establish conditions showing the highest activity of gamma-glutamyl transpeptidase, incubation was performed at various temperatures for 24 hours and 200 rpm.

The example was performed under temperature conditions of 30° C., 37° C. and 40° C., and under the salt concentrations of 0.5% and 5%. After incubation for 24 hours, the supernatant was collected by centrifugation at 8,000 rpm for 20 minutes to measure the enzyme activity.

Figure 5A:
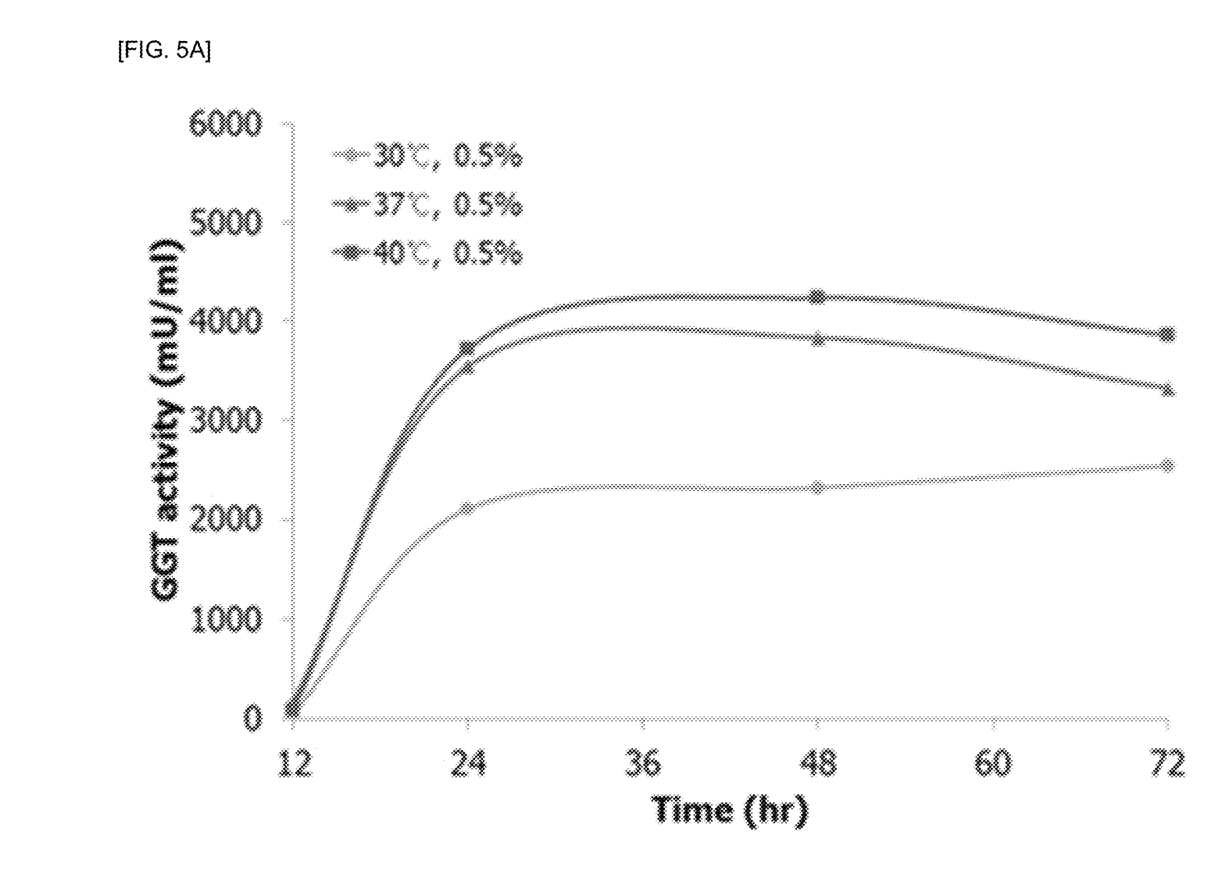
FIG. 5A is a graph showing the activity of gamma-glutamyl transpeptidase produced by the strain of the present invention by temperature in a 0.5% sodium chloride environment
Figure 5B:
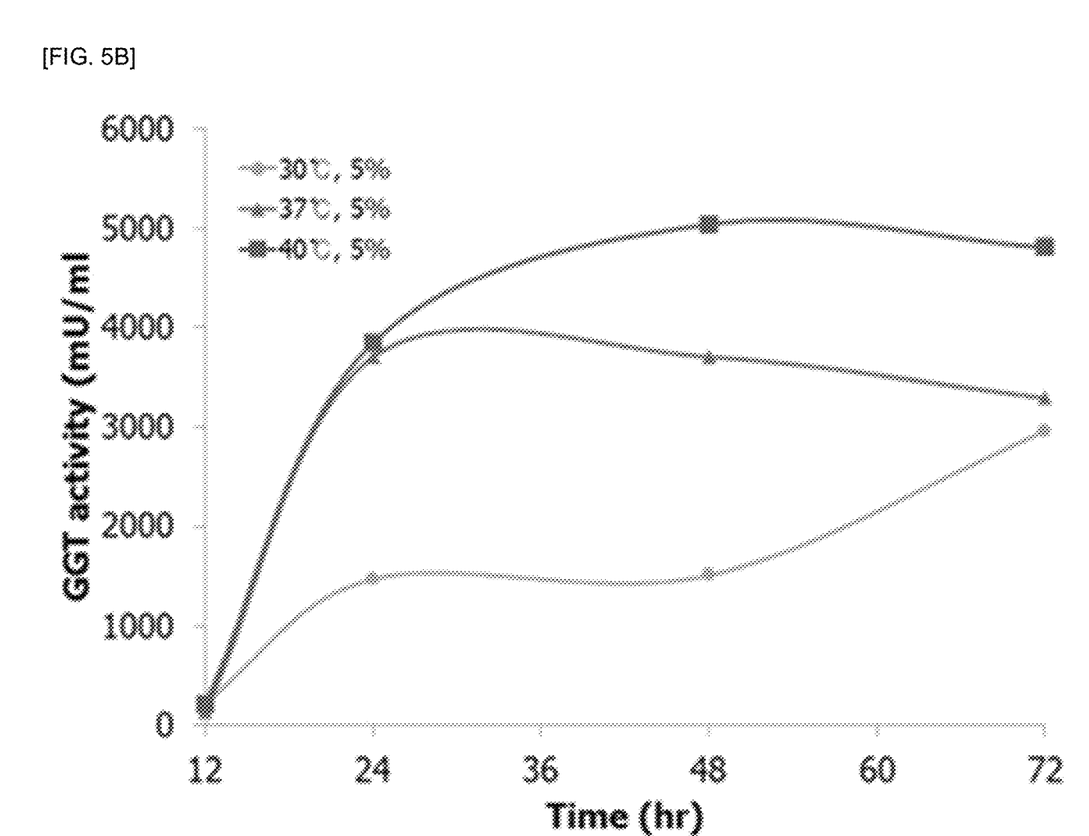
FIG. 5B is a graph showing the activity of gamma-glutamyl transpeptidase produced by the strain of the present invention by temperature in a 5% sodium chloride environment.
Figure 6:
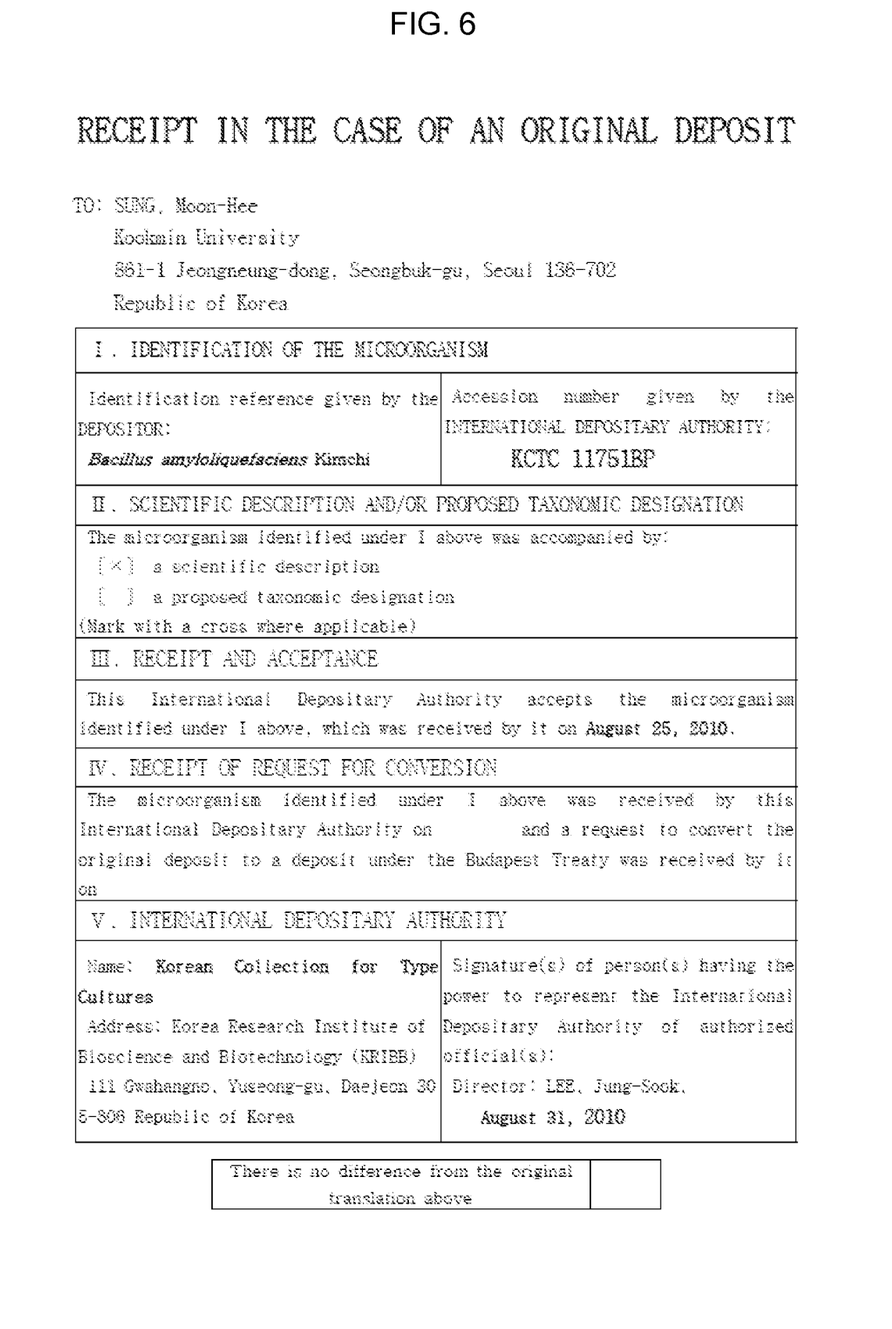
FIG. 6 shows a receipt of an original deposit.
Figure 7:
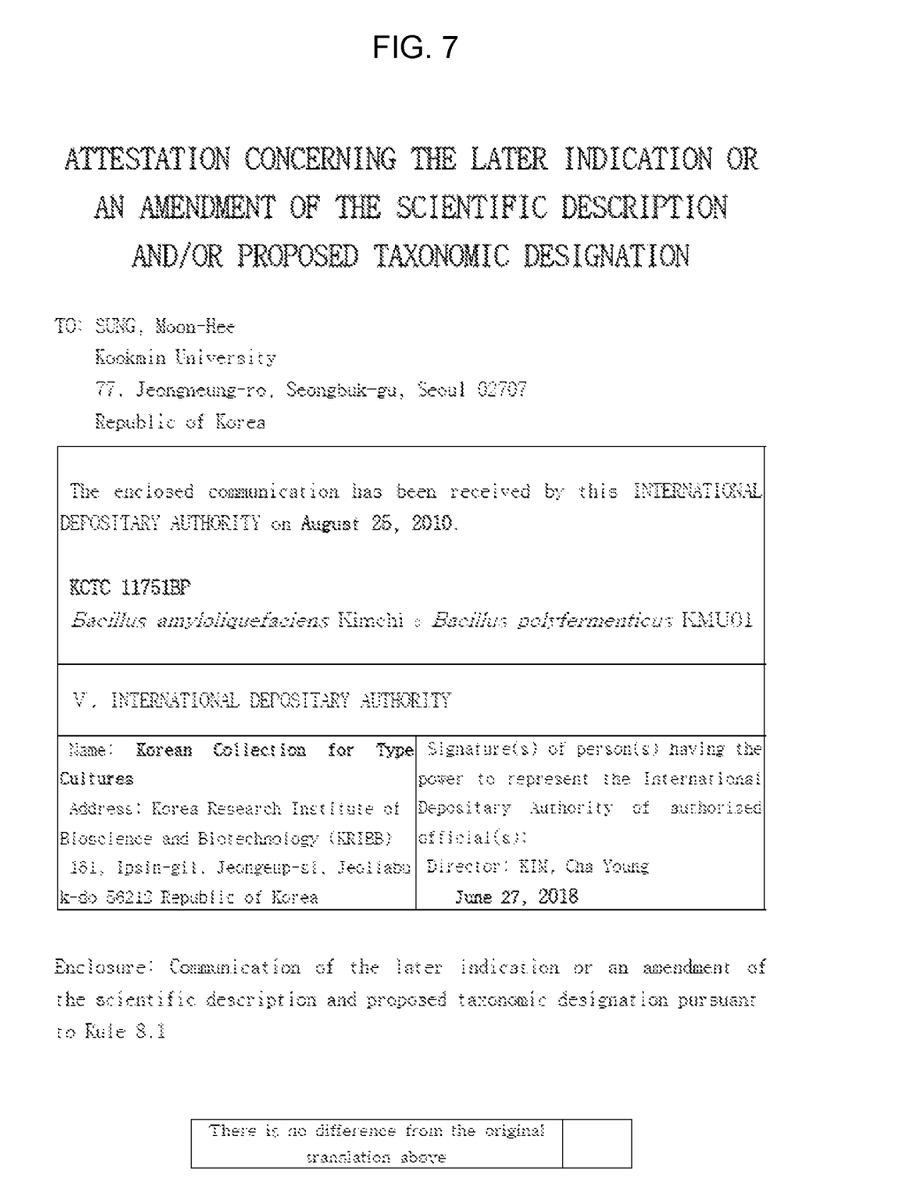
FIG. 7 shows an attestation concerning the later indication or an amendment of the scientific description and/or proposed taxonomic designation.

FIG. 5A shows the enzyme activity according to temperature in a 0.5% sodium chloride environment, and FIG. 5B shows the enzyme activity according to temperature in a 5% sodium chloride environment. The condition showing the maximum gamma-glutamyl transpeptidase enzyme activity is 40° C. and 5% salt. From this, the gamma-glutamyl transpeptidase produced by this strain shows the highest activity at 40° C. and 5% salt, and thus can be called a halophilic enzyme.

While the present invention has been particularly described with reference to specific embodiments thereof, it is apparent that this specific description is only a preferred embodiment and that the scope of the present invention is not limited thereby to those skilled in the art. That is, the practical scope of the present invention is defined by the appended claims and their equivalents.

The invention claimed is:

1. A halophilic *Bacillus polyfermenticus* KMU01 strain producing salt-tolerant gamma-glutamyl transpeptidase.

2. The halophilic *Bacillus polyfermenticus* KMU01 strain of claim 1, wherein the strain is deposited with KCTC11751BP.

3. The halophilic *Bacillus polyfermenticus* KMU01 strain of claim 1, wherein the strain is grown at a concentration of 0.5 to 15% NaCl and a temperature of 30 to 40° C.

4. The halophilic *Bacillus polyfermenticus* KMU01 strain of claim 3, wherein the strain is optimally grown at a concentration of 5% NaCl and a temperature of 40° C.

5. The halophilic *Bacillus polyfermenticus* KMU01 strain of claim 1, wherein the gamma-glutamyl transpeptidase exhibits activity at a concentration of 0.5 to 15% NaCl and a temperature of 30 to 40° C.

6. The halophilic *Bacillus polyfermenticus* KMU01 strain of claim 5, wherein the gamma-glutamyl transpeptidase exhibits highest activity at a concentration of 5% NaCl and a temperature of 40° C.

7. A method of preparing salt-tolerant gamma-glutamyl transpeptidase comprising culturing the halophilic *Bacillus polyfermenticus* KMU01 strain of claim 1.

8. The method of preparing salt-tolerant gamma-glutamyl transpeptidase of claim 7, wherein the strain is cultured at a concentration of 0.5 to 15% NaCl and a temperature of 30 to 40° C.

9. A method of preparing a food composition comprising a bacterial body, comprising culturing the halophilic *Bacillus polyfermenticus* KMU01 strain of claim 1 to prepare the salt-tolerant gamma-glutamyl transpeptidase isolated and purified therefrom, wherein the food compositing contains the salt-tolerant gamma-glutamyl transpeptidase as an active ingredient.

* * * * *